United States Patent [19]

Nakahara et al.

[11] 4,349,468
[45] Sep. 14, 1982

[54] STABILIZER FOR POLYOLEFIN RESIN

[75] Inventors: Yutaka Nakahara, Iwatsuki; Tohru Haruna, Okegawa, both of Japan

[73] Assignee: Adeka Argus Chemical Co., Ltd., Urawa, Japan

[21] Appl. No.: 211,223

[22] Filed: Nov. 28, 1980

Related U.S. Application Data

[63] Continuation of Ser. No. 863,607, Dec. 23, 1977, abandoned.

[51] Int. Cl.$^3$ .................. C07C 149/20; C08K 5/36
[52] U.S. Cl. ........................... 524/302; 260/513 R; 560/152; 544/221
[58] Field of Search ............ 260/45.85 S, 513 R, 260/45.8 NT, 45.95 R, 23 H; 560/152; 544/221

[56] References Cited

U.S. PATENT DOCUMENTS

| | | | |
|---|---|---|---|
| 2,416,052 | 2/1947 | Gribbins | 560/152 |
| 3,629,194 | 12/1971 | Onishi et al. | 260/45.95 R |
| 3,708,543 | 1/1973 | Hickner et al. | 560/152 |
| 3,741,909 | 6/1973 | Yamane et al. | 252/401 |
| 3,758,549 | 9/1973 | Dexter et al. | 260/45.85 H |
| 3,966,675 | 6/1976 | Shurdak | 260/45.8 NT |

FOREIGN PATENT DOCUMENTS 50-106881  8/1975  Japan .

OTHER PUBLICATIONS

Organic Chemistry of Bivalent Sulfur–Reid, vol. 1 (1958) pp. 436 to 453.
Octa Chemica Scandinavica 8 (1954)–Smith et al., pp. 1111-1119.

*Primary Examiner*—V. P. Hoke

[57] ABSTRACT

A new process for preparing a polyhydric alcohol 3-alkylthiopropionate polyolefin resin stabilizer is provided, comprising the steps of heating at 40°–160° C. an alpha-olefin having 6 to 28 carbon atoms with betamercaptopropionic acid or a lower alkyl betamercaptopropionate in the presence of an organic peroxide or azonitrile reaction initiator, esterifying the resulting 3-alkylthiopropionic acid or ester with pentaerythritol or tris(2-hydroxyethyl) cyanurate, and recovering the polyhydric alcohol 3-alkylthiopropionate polyolefin resin stabilizer from the mixture.

Polyolefin resin compositions stabilized with the stabilizer prepared by the process of this invention, and stabilizer compositions comprising the stabilizer prepared by the process of this invention together with a phenol and/or an alkaline earth metal salt of a monocarboxylic acid are also provided.

10 Claims, No Drawings

STABILIZER FOR POLYOLEFIN RESIN

This is a continuation of our application Ser. No. 863,607 of Dec. 23, 1977 now abandoned.

BACKGROUND OF THE INVENTION

This invention relates to a new process for the preparation of polyhydric alcohol 3-alkylthiopropionate ester stabilizers for polyolefin resins. Polyhydric alcohol 3-alkylthiopropionate ester stabilizers have been disclosed previously, but their preparation conventionally has required the use of relatively costly starting materials and furnished products that when used to stabilize polyolefin resins have contributed to the formation of undesirable yellowish and beige discolorations as well as unpleasant odors when the stabilized resins were processed or heat aged at elevated temperatures.

The pioneer disclosure of thioether carboxylic acid esters for stabilizing a polymer is believed to be by M. Gribbins in U.S. Pat. No. 2,519,755 of Aug. 22, 1950. Gribbins stabilized ethylene polymers with 0.001% to 5% by weight of a beta-thioether of an ester of propionic acid having the formula $$ROOCCH_2CH_2S-X,$$

in which R is an alkyl or a cycloalkyl radical such as n- and isobutyl, amyl, heptyl, nonyl, decyl, lauryl, glycyl, cinnamyl, capryl, benzyl, allyl, cetyl, stearyl, palmityl, cyclohexyl, and similar groups, and X is:

1. a hydrocarbon group such as, e.g., the alkyl groups: methyl, ethyl, propyl, butyl, lauryl; the aryl groups: phenyl, naphthyl, benzyl; and such groups as p-methoxy phenyl, p-hydroxyphenyl and cyclohexyl.
2. an oxygenated-hydrocarbon group such as, e.g., the alcohol groups: hydroxymethylene, hydroxyethylene, and hydroxybutylene; the ether groups: methoxymethylene, methoxyethylene and ethoxyethylene; and acid groups and the R esters thereof: carboxymethylene, carboxyethylene, carboxypropylene and carboxybutylene; and aldehyde radicals as aldehydoethyl.
3. a sulfur-hydrocarbon group such as, e.g., mercaptoethyl, mercaptopropyl, mercaptobutyl, mercaptoisobutyl, mercaptohexyl and ethiaethyl.
4. a sulfur-and oxygenated-hydrocarbon group such as, e.g., carboxyethiaethyl ($CH_2CH_2SCH_2CH_2COOH)_2$ carboxyethiaethyldithiaethyl ($CH_2CH_2SSCH_2CH_2SCH_2CH_2COOH$), carboxyethiaisobutyl ($CH_2CH_2CH(CH_3)SCH_2CH_2COOH$) and carboxyethiapropyl ($CH_2CH_2CH_2SCH_2CH_2COOH$).
5. a sulfur-and nitrogen-containing hydrocarbon group such as, e.g., 3-benzothiazyl mercaptopropionic acid, specifically described in U.S. Pat. No. 2,397,960.

Among these, Gribbins found the di-higher alkyl beta-thiodipropionates and especially the dilauryl and distearyl esters outstanding. Subsequently, thioether carboxylic acid esters and in particular thiodipropionates have been employed in conjunction with other stabilizers such as a polyhydric phenol in the stabilization of polypropylene and other polyolefins against degradation upon heating or ageing under atmospheric conditions. Disclosures by C. Tholstrup, U.S. Pat. Nos. 3,033,814 of May 8, 1962 and 3,160,680 of Dec. 8, 1964; L. Rayner, U.S. Pat. No. 3,181,971 of May 4, 1965; D. Bown, U.S. Pat. No. 3,242,135 of Mar. 22, 1966; S. Murdock, U.S. Pat. No. 3,245,949 of Apr. 12, 1966; H. Hagemeyer, U.S. Pat. No. 3,282,890 of Nov. 1, 1966; J. Casey, U.S. Pat. Nos. 3,496,128 of Feb. 17, 1970 and 3,586,657 of June 22, 1971; M. Minagawa, U.S. Pat. Nos. 3,549,572 of Dec. 22, 1970, 3,629,189 of Dec. 21, 1971, 3,673,152 of June 27, 1972, 3,849,370 of Nov. 19, 1974 and 3,869,423 of Mar. 4, 1975; W. Drake U.S. Pat. No. 3,624,026 of Nov. 30, 1971; A. DiBattista, U.S. Pat. No. 3,824,192 of July 16, 1974; B. Cook, U.S. Pat. No. 3,850,877 and H. Mueller U.S. Pat. No. 3,850,918 of Nov. 26, 1974; M. Dexter U.S. Pat. Nos. 3,856,748 of Dec. 24, 1974, 3,888,824 of June 10, 1975, and 3,903,160 of Sept. 2, 1975; P. Klemchuk U.S. Pat. No. 3,860,558 of Jan. 14, 1975; M. Rasberger U.S. Pat. Nos. 3,867,340 of Feb. 18, and 3,901,931 of Aug. 26, 1975; H. Brunetti U.S. Pat. Nos. 3,867,337 of Feb. 18 and 3,873,498 of Mar. 25, 1975; S. Rosenberger U.S. Pat. Nos. 3,884,874 of May 20 and 3,887,518 of June 3, 1975; C. Ramey U.S. Pat. No. 3,907,803 of Sept. 23, 1975 are representative of a very large number of stabilizer combinations including dilauryl and distearyl thiodipropionate or other dialkyl thiodipropionates along with polyhydricphenols and sometimes organic phosphites, metallic stearates, ultraviolet absorbers, nickel compounds, and heavy metal deactivators for use in polypropylene and other polyolefins.

While dialkylthiodipropionates have many favorable attributes such as availability in high purity at reasonable cost, a low degree of toxicity, and generally good stabilizing effectiveness, certain problems attendant on their use have long been recognized, particularly the need to use high concentrations in certain highly stressed formulations to obtain the required heat stability, and a tendency to lose effectiveness in use as a result of exposure to the leaching action of moving streams of warm water and warm air as in the washing and drying cycles of automatic dishwashers and laundry machines.

Attempts to improve on these characteristics have included the use of more efficient and more permanent thiodipropionate esters as well as more effective antioxidants and stabilizer combinations. Thus A. Hecker in U.S. Pat. No. 3,244,650 of Apr. 5, 1966 disclosed a stabilizer system for polypropylene composed of three stabilizers; an organic polyhydric phenol, an organic phosphite and a polyvalent metal salt of an organic acid. To this system, U.S. Pat. No. 3,255,136 of June 7, 1966 added a fourth ingredient, a thiodipropionic acid ester having the formula:

$$R_1OOCCH_2CH_2-S-CH_2CH_2COOY$$

in which $R_1$ is an organic radical selected from the group consisting of hydrocarbon radicals such as alkyl, alkenyl, aryl, cycloalkyl and mixed alkyl aryl and mixed alkyl cycloalkyl radicals; hydroxyalkyl and hydroxyalkyloxyalkylene radicals; and esters thereof with aliphatic carboxylic acids; and Y is selected from the group consisting of (a) hydrogen, (b) a second R radical $R_2$, which can be the same as or different from the $R_1$ radical, (c) a polymeric chain of n thiodipropionic acid ester units:

$$-XO(OCCH_2CH_2SCH_2CH_2COOXO)_nOCCH_2CH_2-S-CH_2CH_2COOZ$$

where Z is hydrogen, $R_2$ or M, n is the number of thiodipropionic acid ester units in the chain, and X is a bivalent hydrocarbon group of the type of $R_1$, that is, alkylene, alkenylene, cycloalkylene, mixed alkylenearylene and mixed alkylene-cycloalkylene radicals: hydroxyalkylene and hydroxyalkyloxyalkylene radicals; and esters thereof with aliphatic carboxylic acids; and (d) a polyvalent metal M of Group II of the periodic table such as zinc, calcium, cadmium, barium, magnesium and strontium.

The molecular weights of the R and Y radicals are taken such that with the remainder of the molecule the thiodipropionic ester has a total of from about ten to about sixty atoms per sulfur atom.

U.S. Pat. No. 3,378,516, patented Apr. 16, 1968 to Tholstrup, Bell and Kibler, proposes combinations including linear thiodi alkanoate polyesters obtained from a thiodialkanoic acid and a diol having a molecular weight of from about 500 to 4000, together with a phenolic antioxidant and/or a phosphite. These combinations are said to display synergistic stabilizing effectiveness.

H. Schirmer in U.S. Pat. No. 3,598,776 of Aug. 10, 1971, disclosed that the incorporation of 10% by weight disproportionated resin in polypropylene enabled him to use 2% by weight dilaurylthiodipropionate (LTP) in the polymer without blooming while in the absence of the rosin only 1% could be used without blooming and the stability of the polymer with the rosin at the higher LTP concentration was significantly increased.

H. Schutze in U.S. Pat. No. 3,630,991 of Dec. 28, 1971 disclosed non-exuding and non-volatile sulfur containing esters of cyclic terpene alcohols for the stabilization of 2 to 8 carbon alpha-olefin polymers together with hindered phenols. Schutze's esters may be represented by the structural formulae $$ROOC\ CH_2(CH)_nSR_a$$

$$ROOC\ CH_2(CH_2)_nSS(CH_2)_nCH_2COOR'$$

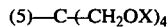
$$ROOCCH_2(CH_2)_nS(CH_2)_nCH_2COOR'$$

$$ROOC\ CH_2(CH_2)_nS(CH_2)_nS(CH_2)_nCH_2COOR'$$

$$ROOC\ CH_2(CH_2)_nS(CH_2)_nS(CH_2)_mCH_3$$

where
$R_a$ is $-CH_2(CH_2)_nCOOR'$ or alkyl n=1 to 5 m=1 to 16

R is a radical selected from the group consisting of abietyl, hydroabietyl, tetrahydroabietyl, dihydroabietyl, dehydroabietyl, dihydropimaryl, tetrahydropimaryl, borneyl, alpha-terpineyl, B-terpineyl, V-terpineyl, methyl, and dihydroterpineyl, and R' is a radical selected from the group consisting of abietyl, hydroabietyl, tetrahydroabietyl, dihydroabietyl, dehydroabietyl, dihydropimaryl, tetrahydropimaryl, borneyl, alpha-terpineyl, B-terpineyl, methyl, and dihydroterpineyl.

A. Onishi, in U.S. Pat. No. 3,629,194 of Dec. 21, 1971 disclosed a polyolefin resin stabilized against thermal aging with esters of alkyl thiopropionic or alkyl thiobutyric acid with a polyol having up to five hydroxyl groups, in combination (optionally) with a phenolic antioxidant. The alkyl thiopropionic or alkyl thiobutyric acid esters are defined as having one of the formulae:

(1) $R-SC_nH_{2n}COOR'OOCC_nH_{2n}SR$ (2) $RSC_nH_{2n}COOC_mH_{2m}SC_mH_{2m}OOCC_nH_{2n}SR$ (3) $R''C(CH_2OX)_3$ (4) 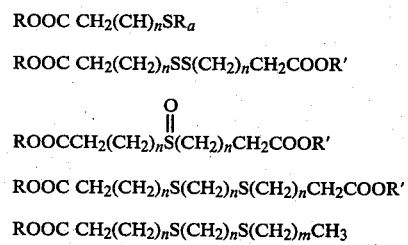

and (5) $-C(CH_2OX)_4$ wherein
R is an alkyl of 8 to 30 carbon atoms,
m and n are each integers of 2 or 3,
R' is an alkylene containing 2 to 12 carbon atoms,
R'' is an alkyl containing 1 to 20 carbon atoms,
X is hydrogen or $-OC-C_nH_{2n}SR$, at least one of which is $-OCC_nH_{2n}SR$,
the $R_1$,R' and R'' moieties in one compound being the same or different.

The phenolic antioxidants are defined by Onishi as mono- or polyhydric phenolic compounds in which at least one of the ortho positions to a hydroxyl group is substituted by an alkyl, aralkyl, or cycloalkyl group.

The substituents preferably contain carbon atoms of a number of the order of 3 to 10, and the alkyl group, inclusive of that in an aralkyl and cycloalkyl groups can be unsaturated. The phenolic compounds may be further substituted, and the phenolic compounds may be polyphenolic compounds such as bisphenolic, trisphenolic, or tetrakisphenolic compounds in which phenolic nuclei are connected by a connecting group such as an alkylene, a thioether, or a triazinoxyl group.

M. Dexter in U.S. Pat. No. 3,758,549 of Sept. 11, 1973 disclosed alkyl esters derived from alkyl thioalkanoic acids and alkane polyols, such as pentaerythritol tetrakis, 3-n-dodecylthiopropionate, and ethylene-bis-3-n-dodecylthiopropionate. These are used in combination with phenolic antioxidants to effectively stabilize polyolefins from the deleterious effects of heat and oxygen. The alkyl esters are defined by the formula:

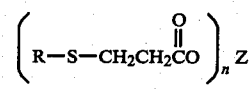

wherein
R is an alkyl group of from one to eighteen carbon atoms,
n has a value of from 2 to 4; and
Z is an aliphatic hydrocarbon of the formula:

$C_yH_{2y+2-n}$ in which y has a value of from 2 to 18 when n is 2 and a value of from 3 to 6 when n is greater than 2, the value of y in all cases being equal to or greater than that of n.

M. Minagawa in Japanese Kokai No. 75/106881 of Aug. 27, 1975 disclosed stabilized resin compositions containing 3-alkylthiopropionate esters of alcohols containing a nitrogen-heterocyclic ring, for example tris(2-hydroxyethyl isocyanurate) and optionally a phenolic antioxidant.

E. Schurdak in U.S. Pat. No. 3,966,675 of June 29, 1976 has disclosed mixtures of pentaerythritol tetrakis (3-n-dodecylthiopropionate) with bis(4-t-butyl-3-hydroxy-2,6-dimethylbenzyl) dithiolterepthalate or 1,3,5-tris(4-t-butyl-3-hydroxy-2,6-dimethylbenzyl)-s-triazine-2,4,6-trione that are stated to be extremely effective in inhibiting the thermal degradation of polypropylene.

SUMMARY OF THE INVENTION

An object of this invention is to provide a polyolefin resin stabilizer comprising a polythioether compound, having no offensive smell such as "mercaptan smell" or "acrylic acid smell" and no possibility of giving a color to the resin and also capable of stabilizing the resin against oxidative degradation for a long period of time.

Another object of this invention is to obtain a polythioether compound having a high polyolefin resin stabilizing effect with no need of undergoing extensive or repeated purification steps.

In accordance with this invention, a polyhydric alcohol 3-alkylthiopropionate polyolefin resin stabilizer capable of enhancing the resistance to deterioration and minimizing the formation of undesirable color and odor of a polyolefin resin when heated at 150° C. and higher is prepared by heating at least one alpha-olefin having 6 to 28 carbon atoms with a betamercaptopropionic acid compound selected from the group consisting of betamercaptopropionic acid and a lower alkyl ester thereof in the presence of a reaction initiator selected from the group consisting of azonitriles and organic peroxides to produce a 3-alkylthiopropionic acid compound, esterifying the 3-alkylthiopropionic acid compound with a polyhydric alcohol selected from the group consisting of pentaerythritol and tris(2-hydroxyethyl)isocyanurate, and recovering the polyhydric alcohol 3-alkylthiopropionate polyolefin resin stabilizer from the reaction mixture.

A preferred technique for recovering the stabilizer from the reaction mixture involves the use of a mixed solvent comprising an aromatic hydrocarbon boiling in the range of 80°-190° C. and a lower aliphatic alcohol, from which the stabilizer having the desired properties is obtained in excellent yield.

Polyolefin resins stabilized with the polyhydric alcohol 3-alkylthiopropionates prepared according to this invention are characterized by excellent heat stability, and retention of good color and odor properties, and include homopolymers and copolymers of alpha-olefins having 2 to 6 carbon atoms, especially polypropylene and polyethylene.

Excellent stabilizer compositions for polyolefin resins comprise the stabilizer prepared according to this invention together with at least one known polyolefin stabilizer, such as a phenol and/or an alkaline earth metal salt of a monocarboxylic acid having 6 to 24 carbon atoms. Such stabilizer compositions contain from 10 to 95 parts by weight of polyhydric alcohol 3-alkylthiopropionate prepared according to this invention, from 5 to 90 parts by weight of a phenol, and from zero to 50 parts by weight of alkaline earth metal salt.

DESCRIPTION OF THE PREFERRED EMBODIMENTS

The alpha-olefin starting materials for the process according to this invention all have the characteristic terminal $=CH_2$ group, and the carbon atom adjacent the terminal $=CH_2$ carries from 1 to 2 alkyl groups. Accordingly, the alpha-olefin can be represented by the formula $RR'C=CH_2$ in which R is an alkyl group, R' is an alkyl group or a hydrogen atom, and the sum of the number of carbon atoms in R and R' is from 4 to 26. Useful alpha-olefins include, for example, hexene-1, 2-methylpentene-1, 4-methylpentene-1, heptene-1, octene-1, 2-ethylhexene-1, nonene-1, decene-1, 2,4,4-trimethylpentene-1, dodecene-1, hexadecene-1, eicosene-1, tetracosene-1, and octacosene-1.

The betamercaptopropionic acid compound can be represented by the formula $HSCH_2CH_2CO_2R''$ where R" is a hydrogen atom or a lower alkyl group such as i-butyl, n-butyl, s-butyl, t-butyl, ethyl, isopropyl, methyl, and n-propyl.

The reaction initiator azonitrile or organic peroxide is used suitably in a concentration of 0.05 to 5 percent by weight of the alpha-olefin and betamercaptopropionic acid compound combined. Larger amounts of reaction initiator can be used but are wasteful and uneconomical.

Useful and preferred azonitrile initiators include 2,2'-azobis-(2-methylpropionitrile), 2,2'-azobis(2-methylbutyronitrile) and 2,2'-azobis(2,4-dimethylvaleronitrile). Useful organic peroxides have 1 to 2 peroxide (-OO-) groups and 4 to 40 carbon atoms and include t-alkyl and aralkyl peroxides such as t-butylhydroperoxide, cumyl-t-butyl peroxide, 2,5-dimethyl-2,5-di(t-butylperoxy hexane), di-t-butylperoxide and dicumyl peroxide; monoperesters such as t-butyl peracetate, t-butylperoxylisobutyrate, t-butylperbenzoate, t-butylperpivalate, t-butylper-2-ethylhexoate, t-butylperoxyneodecanoate, t-butylperlaurate, and mono-t-butylperoxymaleic acid; diperesters such as 2,5-bis(2-ethylhexanoylperoxy)-2,5-dimethylhexane, di-t-butylperoxyphthalate, and 2,5-bis(benzoylperoxy)-2,5-dimethylhexane; aromatic diacyl peroxides such as 2,4-dichlorobenzoylperoxide, benzoyl peroxide and o-toluoylperoxide; Ketone peroxides such as methyl ethyl ketone peroxide, cyclohexanone peroxide, and 1,1-bis(t-butylperoxy)-3,3,5-trimethylcyclohexane; and peroxycarbonate esters such as di-sec-butylperoxydicarbonate, di-t-butylcyclohexylperoxydicarbonate and t-butylperoxyisopropylcarbonate.

A particularly preferred group of organic peroxide initiators consists of aliphatic diacyl peroxides such as acetyl peroxide acetylpropionyl peroxide, acetyl 2-ethylhexanoyl peroxide, 3,5,5-trimethylhexanoylperoxide, lauroyl peroxide, octanoyl peroxide, stearoyl peroxide, propionyl hexacosanoyl peroxide and succinic acid peroxide.

In the reaction of alpha-olefin with betamercaptopropionic acid compound, the reacting proportions of the reactants are one mole of the first to one mole of the second. In carrying out the reaction, the reactants can be mixed in these proportions, but it is sometimes advantageous to use an excess of one reactant and if desired remove and recover the unused portion of such reactant. The reaction is carried out at a temperature within the range of 20°-180° C., preferably 70° to 130° C. Excess betamercaptopropionic acid, when used, can be conveniently removed at the end of the reaction by washing with water. A lower alkyl betamercaptopropionate ester present in excess can be recovered by distillation, suitably under reduced pressure. Alpha-olefin used in excess will be found in the mother liquors after the esterification step when the polyhydric alcohol 3-alkylthiopropionate is recovered.

Once initiated, the reaction of an alpha-olefin with a betamercaptopropionic acid compound is exothermic.

One convenient way to control the reaction is to warm the alpha-olefin and a quantity of the initiator to a temperature where reaction can be intiated, suitably 40°–60° C., remove the heat source, and add betamercaptopropionic acid compound at a rate such that the reaction is sustained until completed by the exothermic effort.

Another useful method is to premix betamercaptopropionic acid compound and alpha-olefin at 40°–60° C. and add quantities of reaction initiator from time to time until analysis shows the consumption of mercaptopropionic acid compound to be complete. If desired, any unreacted mercaptopropionic acid compound can then be removed from the 3-alkylthiopropionic acid compound produced before continuing to the esterification step.

The preparation of the 3-alkylthiopropionic acid or a lower alkyl ester thereof by the reaction of an alpha-olefin and beta-mercaptopropionic acid or a lower alkyl ester thereof can be accomplished either in the absence or in the presence of a solvent, and in the latter case, it is desirable to use a hydrocarbon solvent such as ligroin or toluene. The esterification of the 3-alkylthiopropionic acid compound with pentaerythritol and/or tris(2-hydroxyethyl)isocyanurate can be carried out by heating the reactants together at 60°–220° C. The esterification reaction can be helped to completion by removal of the side product water or lower alkanol, by the use of an esterification catalyst, or by both of these expedients in combination. Water or lower alkanol produced during the esterification can be removed by distillation, assisted by application of vacuum, by sparging with a gas, or by the use of a boiling inert solvent. Esterification catalysts that can be used include strong acids, bases, and multivalent metal compounds, for example sulfuric acid, ethanesulfonic acid, sodium methoxide, potassium bicarbonate, zinc chloride, aluminum, titanium, and zirconium butoxides, and di-n-octyltin oxide.

The relative proportions of polyhydric alcohol and 3-alkylthiopropionic acid compound used in the esterification reaction are usually approximately those determined by the composition of the ester being prepared, i.e. triester & tetraester of pentaerythritol or diester & triester of tris(2-hydroxyethyl) isocyanate, although an excess of either the polyhydric alcohol or the 3-alkylthiopropionic acid compound can be used if desired when the unreacted portions of the reactant can be tolerated in the finished product or conveniently removed.

The polyhydric alcohol 3-alkylthiopropionate produced by the process of this invention can be isolated from the reaction mixture in which it is obtained by conventional techniques such as stripping of volatile reactants and by-products, suitably under reduced pressure, away from the desired product; crystallization from a suitable solvent, directly or after stripping; or separation from undesired impurities by enriching the desired product in one of a pair of immiscible liquids, for example the pair hexane and 80% aqueous methanol. A particularly preferred and convenient method for recovering polyhydric alcohol 3-alkylthiopropionate according to this invention comprises the use of a solvent mixture containing an aromatic hydrocarbon having an atmospheric boiling point in the range from 80° to 190° C. and a lower aliphatic alcohol. Suitable aromatic hydrocarbons include benzene, toluene, ethylbenzene, o-, m-, and p-xylene, cumene, p-cymene, trimethylbenzenes, ethylmethyl-benzenes, diethylbenzenes, and mixtures thereof. Suitable lower alcohols include the isomeric butyl, ethyl, methyl and propyl alcohols and mixtures thereof. An especially preferred solvent mixture comprises toluene and methanol.

The preparation of pentaerythritol tris(3-alkylthiopropionate), pentaerythritol tetrakis (3-alkylthiopropionate) and tris(3-alkyl-thiopropionyloxyethyl) isocyanurate polyolefin resin stabilizers by a process of this invention can be summarized by the following Scheme of reaction equations in which R, R′, and R″ are as previously defined.

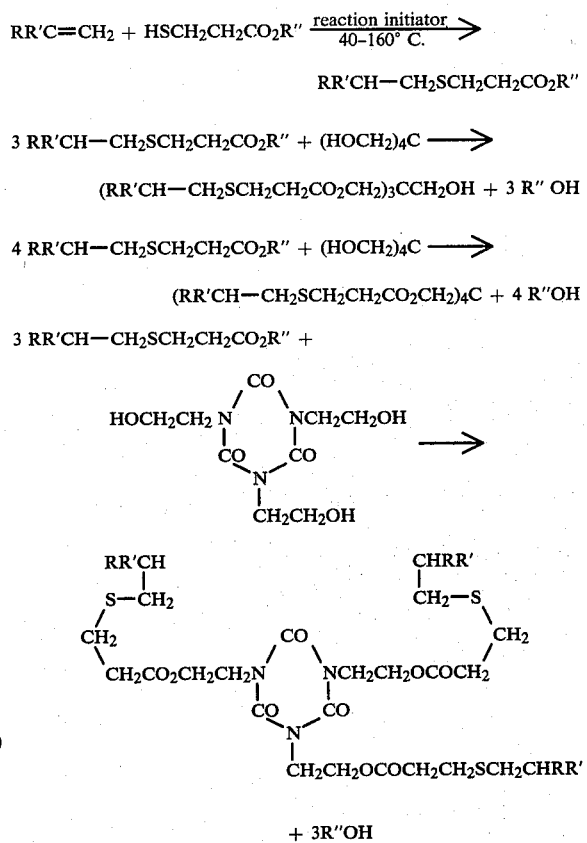

+ 3R″OH

Illustrative polyhydric alcohol 3-alkylthiopropionates prepared by a process of this invention are shown by name and formula.

1,3,5-Tris(n-hexylthiopropionyloxyethyl)isocyanurate

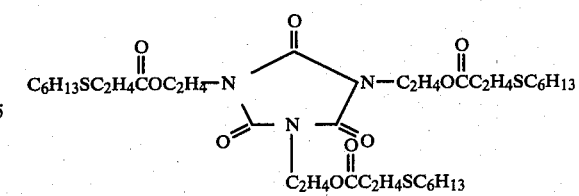

1,3,5-Tris(n-dodecylthiopropionyloxyethyl)isocyanurate

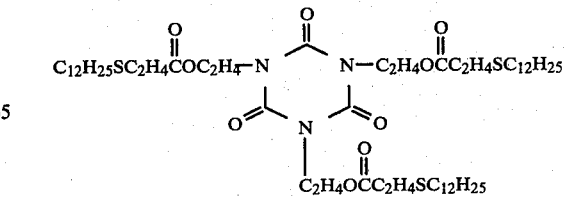

-continued 1,3-Bis(n-octadecylthiopropionyloxyethyl)-5-hydroxyethyl isocyanurate

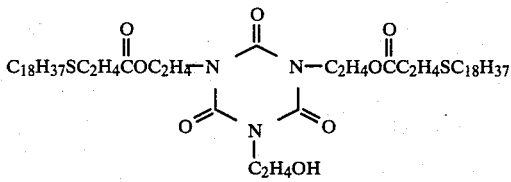

Pentaerythritol tetrakis (3-n-octylthiopropionate)

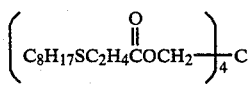

Pentaerythritol tetrakis (3-n-dodecylthiopropionate)

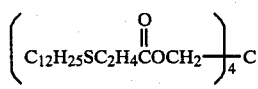

Pentaerythritol tetrakis (3-n-octadecylthiopropionate)

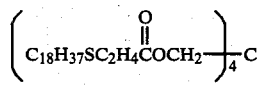

Synthetic Examples 1 through 6 below provide a detailed description of the preparation of certain polyhydric alcohol 3-alkylthiopropionate stabilizers by a process according to this invention.

SYNTHETIC EXAMPLE—1

C-(CH$_2$OOCC$_2$H$_4$S—C$_{16-18}$ alkyl)$_4$ 53 g (0.5 mol) of beta-mercaptopropionic acid was heated to 70° C. and then the mixture of 116.0 g (0.505 mol) of alpha-olefin (C$_{16-18}$, DIALEN 168: Mitsubishi Chemical) and 1.6 g of lauroyl peroxide was added dropwise. Because exothermic heating occurred, addition rate was controlled so as not to exceed 120° C. in the reaction mixture. After addition, the reaction was continued for 7 hours at 110° C. Then 17.0 g (0.125 mol) of pentaerythritol, 0.2 g of p-toluenesulfonic acid (pts) and 300 ml of toluene were added. The mixture was heated and stirred, and produced water was distilled out. After 9 ml of water was distilled, the solution was cooled to room temperature. 166 g of pentaerythritol tetrakis(3-alkyl(C$_{16-18}$)thiopropionate), 94.3% of theroetical yield white powder was obtained by adding a large amount of methanol to the solution. (Sample No. 1: M.P. 62°-64° C.)

SYNTHETIC EXAMPLE—2

C-(CH$_2$OOCC$_2$H$_4$S-C$_{12-14}$ alkyl)$_4$ 53 g (0.5 mol) of betamercaptopropionic acid was heated to 70° C. and then 91.4 g (0.505 mol) of alpha-olefin (C$_{12-14}$, DIALEN 124) containing dissolved 1.4 g of lauroyl peroxide was added dropwise. Because exothermic heating occurred, addition was controlled so as not to exceed 120° C. in the reaction mixture. After addition, the reaction was continued for 7 hours at 110° C. Then 17.0 g (0.125 mol) of pentaerythritol, 0.2 g of pts and 300 ml of toluene were added. The mixture was heated and stirred, and produced water was distilled out. After 9 ml of water was distilled, the solution was cooled to room temperature. 140 g of white powder was obtained by adding methanol to the solution, (Sample No. 2: M.P. 46°-51° C.) representing a 92.4% yield of pentaerythritol tetrakis(3-alkyl(C$_{12-14}$)thiopropionate).

SYNTHETIC EXAMPLE—3

C-(CH$_2$OOCC$_2$H$_4$SC$_{18}$H$_{37}$)$_4$ 53 g (0.5 mol) of beta-mercaptopropionic acid was heated to 70° C., and then 123.6 g (0.505 mol) of octadecene containing dissolved 1.7 g of 2,2'-azobisisobutyronitrile was added dropwise. Because exothermic heating occurred, addition was controlled so as not to exceed 120° C. in the reaction mixture. After addition, the reaction was continued for 7 hours at 110° C. Then 17.0 g (0.125 mol) of pentaerythritol, 0.2 g of pts and 300 ml of toluene was added. The whole was heated and stirred, and produced water was distilled out. After 9 ml of water was distilled, the solution was cooled to room temperature. 171.5 g of white powder was obtained by adding methanol to the solution, (Sample No. 3: M.P. 64.5°-66.5° C.) representing a 93.5% yield of pentaerythritol tetrakis(3-octadecylthiopropionate).

SYNTHETIC EXAMPLE—4

C-(CH$_2$OOCC$_2$H$_4$S-C$_{16-18}$ alkyl)$_4$ 60 g (0.5 mol) of methyl-beta-mercaptopropionate was heated to 70° C., and then 116.6 g (0.505 mol) of alpha-olefin (DIALEN 168) containing dissolved 1.7 g of lauroylperoxide was added dropwise. Because exothermic heating occurred, the rate of addition was controlled so as not to exceed 120° C. in the reaction mixture. After addition, the reaction was continued for 7 hours at 110° C. Then, 17.0 g (0.125 mol) of pentaerythritol and 0.9 g of sodiummethoxide was added.

The whole was reacted for 7 hours at 100°-110° C. under a nitrogen stream.

After cooling to room temperature, toluene was added and the whole was passed through a bed of alumina. 168 g of white powder was obtained by adding methanol to the solution, (Sample No. 4: M.P. 62°-64° C.) representing a 95% yield of pentaerythritol tetrakis (3-alkyl(C$_{16-18}$)thiopropionate).

SYNTHETIC EXAMPLE—5

Tris(3-octadecylthiopropionyloxyethyl)isocyanurate 53 g (0.5 mol) of beta-mercaptopropionic acid was heated to 70° C., and then 123.6 g (0.505 mol) of octadecene containing dissolved 1.7 g of lauroylperoxide was added dropwise. Because exothermic heating occurred, the rate of addition was controlled so as not to exceed 120° C. in the reaction mixture. After addition, the whole was stirred for 7 hours at 110° C. Then, 43.6 g (0.167 mol) of tris (2-hydroxyethyl) isocyanurate, 0.2 g of pts and 300 ml of toluene were added and the whole was heated and stirred. The produced water was distilled out and after 9 ml of water was distilled, the whole was cooled to room temperature. 198.5 g of white powder was obtained by adding methanol to the solution, (Sample No. 5 M.P. 75°–77° C.) representing 94.6% of theoretical yield.

SYNTHETIC EXAMPLE—6

Tris(3-$C_{16-18}$ alkylthiopropionyloxyethyl)isocyanurate 53 g (0.5 mol) of beta-mercapto propionic acid was heated to 70° C., and then 116.6 g (0.505 mol) of alpha-olefin (DIALEN 168) containing dissolved 1.7 g of lauroyl peroxide was added dropwise. Because exothermic heating occurred, the rate of addition was controlled so as not to exceed 120° C. in the reaction mixture. After addition, the whole was stirred for 7 hours at 110° C. Then 43.6 g (0.167 mol) of tris(2-hydroxyethyl) isocyanurate, 0.2 g of pts and 300 ml of toluene were added and the produced water was distilled out. After 9 ml of water was distilled, the solution was cooled to room temperature. 190.5 g of white powder was obtained by adding methanol to the solution, (Sample No. 6 M.P. 72°–76° C.) representing 94.2% of theoretical yield.

SYNTHETIC EXAMPLE—7

$C(CH_2OOCC_2H_4S(CH_2)_{11}CH_3)_4$ 21.2 g (0.2 moles) of beta-mercaptopropionic acid, 40.3 g (0.24 moles) of 1-dodecene and 0.06 g of azobisisobutyronitrile were put into a flask and the mixture was agitated at 70° C. for 1 hour in a nitrogen stream, followed by additional 3-hour agitation at 80° C., and then the mixture was further heated under reduced pressure to distill off the excess quantity of dodecene under the conditions of maximum 120° C./2 mm Hg. Upon cooling of the product, there was obtained white solid 3-laurylthiopropionic acid (M.P.: 60°–62° C.).

This product was then mixed with 6.8 g (0.05 moles) of pentaerythritol, 0.06 g of p-toluenesulfonic acid with the generated water being removed. When 3.6 ml of generated water was distilled out, the reaction was stopped and the reaction product, after cooling, was mixed with methanol to obtain 54.7 g of white powder with melting point of 44° to 47° C. (Sample no. 7) representing a 96.8% yield of pentaerythritol tetrakis (3-laurylthiopropionate)

COMPARATIVE SYNTHETIC EXAMPLE—1

$C-(CH_2OOCC_2H_4SC_{12}H_{25})_4$

To a mixture of 101 g (0.5 mol) of n-lauryl mercaptan and 0.5 g of $NaOCH_3$ was added 68.4 g (0.8 mol) of methyl acrylate at 25°–30° C. through about 1 hour. After addition, the reaction was continued for 15 hours at 25°–30° C. and 67.0 g of methyl-3-n-laurylthiopropionate was obtained by distillation (151°–153° C./0.3 mm Hg). 57.6 g (0.2 mol) of this ester, 6.5 g (0.048 mol) of pentaerythritol and 0.25 g of $NaOCH_3$ were reacted for 7 hours at 100°–110° C. under a nitrogen stream. After cooling to room temperature, toluene was added and the whole was passed through a bed of alumina. 54.3 g of white powder was obtained by adding methanol to the solution, (Comparative Sample No. 1: M.P. 45°–47° C.) representing a 97.5% yield of pentaerythritol tetrakis (3-n-laurylthiopropionate).

COMPARATIVE SYNTHETIC EXAMPLE—2

Tris(3-n-laurylthiopropionyloxyethyl)isocyanurate 57.6 g (0.2 mol) of methyl-3-n-laurylthiopropionate prepared by the same procedure as comparative synthetic example -1, 15.6 g (0.06 mol) of tris (2-hydroxy ethyl) isocyanurate and 0.25 g of $NaOCH_3$ were reacted for 7 hours at 100°–110° C. under nitrogen stream. After cooling, toluene was added and the whole was passed through a bed of alumina. 66.5 g of white powder was obtained by adding methanol to the solution, (Comparative sample no. 2 M.P. 66°–68° C.) representing a 95.3% yield of tris(3-n-laurylthiopropionyloxyethyl)isocyanurate.

Polyolefin resins that can be stabilized with polyhydric alcohol 3-alkylthiopropionates prepared by a process of this invention include polymers of olefins having two to six carbon atoms such as polyethylene, polypropylene, poly-1-butene, poly-3-methylbutene, poly-4-methylpentene, poly-1-hexane, and copolymers of these olefins, particularly copolymers of ethylene with propylene, butene-1, or hexene-1, as well as blends of two or more of these polyolefins, and alpha-olefin copolymers such as ethylene-vinyl acetate copolymers, ethylene-ethyl acrylate copolymers, and ethylenepropylene-diene terpolymers. They also include olefin resins and copolymers crosslinked by heating with a peroxide or by exposure to ionizing radiation, and foamed polyolefins which are foamed by a blowing agent.

Stabilizer compositions comprising a polyhydric alcohol 3-alkylthiopropionate prepared by a process of this invention together with a polyolefin resin stabilizer such as a phenol and/or alkaline earth metal salt of a monocarboxylic acid having 6 to 24 carbon atoms can be formulated and marketed in liquid, solid and paste forms. An inert solvent can be used to facilitate handling. The components can also be solubilized in one another by heating, such as at 70°–160° C. for up to 4 hours, and then allowing the resulting melt to cool and harden sufficiently to be flaked and ground.

A stabilizer prepared according to this invention is added to the polyolefin resins such as mentioned above to improve their oxidative stability in an amount of 0.01 to 5 weight parts, preferably 0.05 to 3 weight parts, per 100 weight parts of the resin.

Incorporation of a phenol in the stabilizer composition of this invention produces an excellent synergistic effect enhancing the effectiveness of the polyhydric alcohol 3-alkylthiopropionate stabilizer.

As examples of the phenols suited for use in this invention, one may cite the following: 2,6-di-tertiary butyl-p-cresol, stearyl-(3,5-di-methyl-4-hydroxybenzyl) thioglycolate, stearyl-beta-(4-hydroxy-3,5-di-tertiary butylphenyl) propionate, distearyl-(4-hydroxy-3-methyl-5-tertiary butyl) benzylmalonate, 2,2'-methylenebis(4-methyl-t-tertiary butylphenol), 4,4'-methylenebis(2,6-di-tertiary butylphenol), 2,2'-methylene bis(6-(1-methylcyclohexyl)-p-cresol), bis(3,3-bis(4-hydroxy-3-tertiary butylphenyl) butyric acid) glycol ester, 4,4'-butylidenebis(6-tertiary butyl-m-cresol), 1,1,3-tris(2-methyl-4-hydroxy-5-tertiary butylphenyl)-butane, 1,3,5-tris(3,5-di-tertiary butyl-4-hydroxybenzyl)-2,4,6-trimethylbenzene, tetrakis(methylene-3-(3,5-di-tertiary butyl-4-hydroxyphenyl) propionate)methane, 1,3,5-tris(3,5-di-tertiary butyl-4-hydroxybenzyl)isocyanurate, 1,3,5-tris(3,5-di-tertiary butyl) 4-hydroxyphenyl) propionyloxyethyl) isocyanurate, 2-octylthio-4,6-di(4-hydroxy-3,5-di-tertiary butyl) phenoxy-1,3,5-triazine, and 4,4'-thiobis(6-tertiary butyl-m-cresol).

A comprehensive disclosure of useful phenols by M. Minagawa et al in U.S. Pat. No. 3,907,517 column 17 line 64 to column 23 line 61 is here incorporated by reference. When phenols are used, the concentration per 100 parts of polyolefin resin can range from 0.01 to about 0.5 part by weight.

The stabilizer according to this invention, when mixed with a photostabilizer, can improve light resistance of the resin.

Among the photostabilizers usable for the said purpose in this invention are, for example, benzophenones such as 2-hydroxy-4-methoxybenzophenone and 2-hydroxy-4-octoxybenzophenone, esters such as p-tertiary butylphenyl salicylate and 2,4-di-tertiary butylphenyl-3',5'-di-tertiary butyl-4'-hydroxy-benzoate, hydroxyphenyl benzotriazoles such as 2-(2'-hydroxy-5'-methylphenyl)benzotriazole and 2-(2'-hydroxy-3',5'-di-tertiary butylphenyl)-5-chlorobenzotriazole, piperidines such as bis(2,2,6,6-tetramethyl-4-piperidinyl)sebacate, and nickel complex salts.

It is also possible to mix in the stabilizer of this invention metallic soaps of the alkaline earth metals, antistatic agents, phosphite compounds, flame retardants, processing aids, metal inactivating agents, nucleating agents, epoxy compounds, lubricants, fillers, pigments, plasticizers, fluorescent agents, expanding agents and the like.

Representative alkaline earth metal salts of monocarboxylic acids having 6 to 24 carbon atoms include calcium 2-ethylbutyrate, strontium caproate, barium benzoate, calcium-p-t-butylbenzoate, strontium laurate, barium myristate, calcium palmitate, strontium behenate, and barium linoleate. Additional alkaline earth metal salts of monocarboxylic acids having 6 to 24 carbon atoms are included among those disclosed by M. Minagawa in U.S. Pat. No. 3,869,423, column 9 line 56 to column 20 line 35. The concentration of alkaline earth metal salt based on 100 parts of polyolefin resin can range from zero to about 1 part by weight. The preparation of stabilized polyolefin resin compositions according to this invention is easily accomplished by conventional procedures. A heated two roll mill, for example, is a convenient compounding tool for blending stabilizer compositions of the invention with polyolefin resins.

EXAMPLE 1

Unstabilized polypropylene resin (Profax 6501) 100 parts by weight, Ca-stearate 0.2 part, stearyl-beta-(3,5-di-t-butyl-4-hydroxyphenyl) propionate 0.1 part and sample compound 0.3 part were compounded by grinding and mixing 10 minutes. The compounded mixture was kneaded on a two roll mill at 180° C. for 6 minutes to give a rough sheet and then a polished sheet of 1.0 mm in thickness was prepared by compression molding at 180° C., and 200 kg/cm$^2$ for 5 minutes. Test pieces of 10×20 mm were cut off from this sheet and the heat aging test was carried out on aluminum foils in a Geer oven at 160° C. in an air atmosphere and, the coloring of the sheets and the odor of the sample compounds were observed. The results are shown in Table-1.

TABLE 1

| No. | Sample Compound | 160° C. Oven Heat Stability, Hours to Failure | Color of Sheet | Odor of Sample |
|---|---|---|---|---|
| Control |  |  |  |  |
| 1-1 | Dilaurylthiodipropionate comparative sample | 570 | Very pale Yellow | None |
| 1-2 | Comparative Sample No. 1 | 675 | Pale Yellow | Strong |
| 1-3 | Comparative Sample No. 2 | 690 | Very Pale Yellow | Moderate |
| EXAMPLE |  |  |  |  |
| 1-1 | Sample No. 1 | 980 | None | None |
| 1-2 | Sample No. 2 | 965 | None | None |
| 1-3 | Sample No. 3 | 970 | None | None |
| 1-4 | Sample No. 4 | 970 | None | None |
| 1-5 | Sample No. 5 | 985 | None | None |
| 1-6 | Sample No. 6 | 1,020 | None | None |
| 1-7 | Sample No. 7 | 1,005 | None | None |

The results of the test show the surprisingly advantageous heat stability, color, and odor properties obtained with samples of polyhydric alcohol 3-alkylthiopropionates prepared by a process of this invention.

EXAMPLE—2

Sheets of 0.5 mm in thickness were prepared according to the following formulation.

The heating test was carried out in a Geer oven at 160° C. The yellowness of the sheets after irradiating 64 hours with fluorescent light were measured by Hunter color meter. The results are shown in Table-2.

TABLE 2

| (FORMULATION) | |
|---|---|
| Unstabilized polypropylene resin | 100 parts |
| 1,1,3-tris-(2-methyl-5-t-butyl-4-hydroxyphenyl)butane | 0.1 |
| Sample compound | 0.3 |

| No. | Sample Compound | 160° C. Oven Heat Stability, Hours to Failure | Yellowness |
|---|---|---|---|
| Control |  |  |  |
| 2-1 | Distearylthiodipropionate | 480 | 0.21 |
| 2-2 | Comparative Example No. 1 | 830 | 0.18 |
| 2-3 | Comparative Example No. 2 | 810 | 0.17 |
| EXAMPLE |  |  |  |
| 2-1 | Sample No. 1 | 1,130 | 0.12 |
| 2-2 | Sample No. 2 | 1,060 | 0.11 |
| 2-3 | Sample No. 3 | 1,170 | 0.12 |
| 2-4 | Sample No. 4 | 1,040 | 0.13 |
| 2-5 | Sample No. 5 | 1,100 | 0.12 |
| 2-6 | Sample No. 6 | 1,150 | 0.12 |
| 2-7 | Sample No. 7 | 1,120 | 0.11 |

The results of this test show the surprisingly favorable heat and color stability of polypropylene containing polyhydric alcohol 3-alkylthiopropionates prepared according to this invention.

EXAMPLE—3

Stabilized polyethylene resin (Hizex 5100E) 100 parts by weight and sample compound 0.15 part were kneaded on a two roll mill at 150° C. for 5 minutes, and then a sheet of 1.2 mm in thickness was prepared by compression molding at 150° C., and 180 kg/cm$^2$, for 5 minutes. Test pieces of 10×20 mm were cut off from this sheet and the heating test was carried out on aluminum-foils in a Geer oven at 150° C. in an air atmosphere.

Ten pieces of each sample were used and the time when more than five pieces of a sample were discolored and waxy, was taken as the beginning time of deterioration. The results are shown in Table-3.

TABLE 3

| No. | SAMPLE COMPOUND | BEGINNING TIME OF DETERIORATION |
| --- | --- | --- |
| Control | | |
| 3-1 | NONE | 183 hours |
| 3-2 | Comparative Sample No. 1 | 314 |
| 3-3 | Comparative Sample No. 2 | 337 |
| EXAMPLE | | |
| 3-1 | Sample No. 1 | 482 |
| 3-2 | Sample No. 2 | 470 |
| 3-3 | Sample No. 3 | 466 |
| 3-4 | Sample No. 4 | 457 |
| 3-5 | Sample No. 5 | 465 |
| 3-6 | Sample No. 6 | 491 |
| 3-7 | Sample No. 7 | 486 |

The results of this test demonstrate the surprisingly favorable effect of polyhydric alcohol 3-alkylthiopropionates on the heat stability of polyethylene.

We claim:

1. A pentaerythritol tetrakis (3-laurylthiopropionate) polyolefin stabilizer capable of enhancing the resistance to deterioration and minimizing the formation of undesirable color and odor of a polyolefin resin when heated at 150° C., produced by a process comprising the steps of heating an alpha-olefin having twelve carbon atoms with a beta-mercaptopropionic acid compound selected from the group consisting of beta-mercaptopropionic acid and a lower alkyl ester thereof in the presence of 0.05 to 5 percent by weight of the alpha-olefin and beta-mercaptopropionic acid compound combined of a reaction initiator selected from the group consisting of azonitriles and peroxides to produce a 3-laurylthiopropionic acid compound, esterifying the 3-laurylthiopropionic acid compound with pentaerythritol, and recovering the pentaerythritol 3-laurylthiopropionate polyolefin resin stabilizer from the mixture.

2. A polyolefin resin stabilizer according to claim 1 in which the beta-mercaptopropionic acid compound of the process is beta-mercaptopropionic acid.

3. A polyolefin resin stabilizer according to claim 1 in which the reaction initiation of the process is 2,2'-azobis(2-methylpropionitrile).

4. A polyolefin resin stabilizer according to claim 1 in which the reaction initiator of the process is an aliphatic diacyl peroxide having 4 to 40 carbon atoms.

5. A polyolefin resin stabilizer according to claim 1 in which the reaction initiator of the process is lauroyl peroxide.

6. A polyolefin resin stabilizer according to claim 1 which is recovered from a solution comprising an aromatic hydrocarbon and a lower alcohol.

7. A stabilizer composition capable of enhancing the resistance to deterioration and minimizing the formation of undesirable color and odor of a polyolefin resin when heated at 150° C., comprising a stabilizer according to claim 1 and at least one polyolefin stabilizer selected from the group consisting of phenols and alkaline earth metal salts of monocarboxylic acids having 6 to 24 carbon atoms.

8. A polyolefin resin composition having enhanced resistance to deterioration and minimized tendency to form undesirable color and odor when heated at 150° C., comprising a polyolefin resin and a stabilizer according to claim 1.

9. A polyolefin resin composition according to claim 8 in which the polyolefin resin is polypropylene.

10. A polyolefin resin composition according to claim 8 in which the polyolefin resin is polyethylene.

* * * * *